United States Patent [19]

Williams et al.

[11] Patent Number: 4,906,658

[45] Date of Patent: Mar. 6, 1990

[54] FLUORO-SULFONES

[75] Inventors: Haydn W. R. Williams, Dollard des Ormeaux; Robert N. Young, Senneville, both of Canada

[73] Assignee: Merck Frosst Canada, Inc., Quebec, Canada

[21] Appl. No.: 41,015

[22] Filed: Apr. 21, 1987

[51] Int. Cl.$^4$ .................. A61K 31/19; A61K 31/365; C07C 147/06; C07C 147/11

[52] U.S. Cl. .................... 514/473; 514/570; 514/826; 514/861; 514/863; 514/886; 514/887; 514/893; 514/914; 549/323; 562/426; 562/429; 568/314; 568/315; 568/322; 568/337

[58] Field of Search ............... 562/429; 514/545, 570, 514/473, 826, 861, 863, 886, 887, 914, 893; 549/323; 560/11

[56] References Cited

U.S. PATENT DOCUMENTS 4,148,915 4/1979 Thuillier .............................. 562/429
4,486,223 12/1984 Konishi et al. ..................... 562/429

FOREIGN PATENT DOCUMENTS 1108683 6/1961 Fed. Rep. of Germany ...... 562/429
2545947 4/1977 Fed. Rep. of Germany ...... 562/429
212137 12/1982 Japan .................................. 562/429

Primary Examiner—Vivian Garner
Attorney, Agent, or Firm—Gabriel Lopez; Hesna J. Pfeiffer

[57] ABSTRACT

Compounds of Formula I

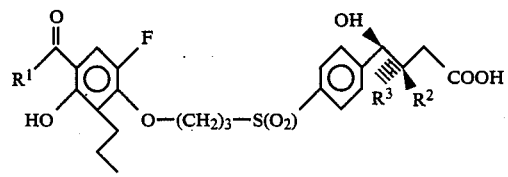

the pharmaceutically acceptable salts, and the gamma-lactone form thereof are described. They are antagonists of leukotrienes and SRS-A.

6 Claims, No Drawings

FLUORO-SULFONES

BACKGROUND

Leukotriene antagonists of the formula:

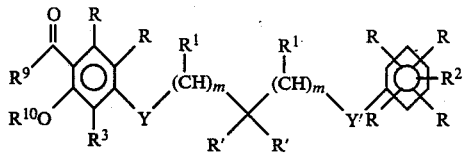

are described in EP No. 104,885 as leukotriene antagonists.

The leukotrienes and their biological activities, especially their roles in various disease states and conditions have been described. For example, see EP No. 140,684 (May 8, 1985), which is incorporated herein by reference.

SUMMARY

It has now been found that compounds of Formula I, especially the species (4R*,3S*)-4-[4-(3-(4-acetyl-6-fluoro-3-hydroxy-2-propylphenoxy)propyl- sulfonyl)-phenyl]-4-hydroxy-3-methylbutanoic acid, are unexpectedly much more potent as antagonists of leukotrienes $C_4$, $D_4$ and $E_4$ and of SRS-A than closely related compounds within the scope of EP No. 104,885.

The present invention relates to compounds having activity as leukotriene and SRS-A antagonists, to methods for their preparation, to intermediates useful in their preparation and to methods and pharmaceutical formulations for using these compounds in mammals (especially humans).

Because of their activities as leukotriene and SRS-A antagonists, the compounds of the present invention are useful as anti-asthmatic, antiallergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compound of the present invention is of the formula:

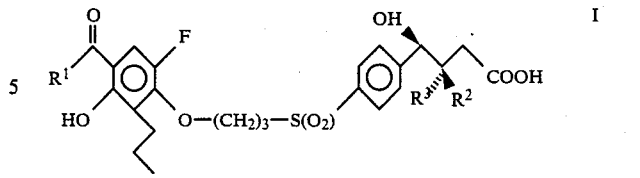

wherein:
$R^1$ is $C_1$–$C_6$ alkyl;
$R^2$ is H or $C_1$–$C_6$ alkyl;
$R^3$ is H or $C_1$–$C_6$ alkyl; and
the pharmaceutically acceptable salts and the γ lactone form thereof.

A preferred embodiment of I is that wherein:
$R^1$ is $C_1$–$C_6$ alkyl;
$R^2$ is $C_1$–$C_6$ alkyl;
$R^3$ is H; and
both OH and $R^2$ are on the same side of the $C_3$–$C_4$ bond, i.e., where OH and $R^2$ have the relative stereochemical relationship 4R*, 3S*.

Particularly preferred is (4R*, 3S*)-4-[4-(3-(4-acetyl-6-fluoro-3-hydroxy-2-Propylphenoxy)propylsulphonyl)phenyl]-4-hydroxy-3-methylbutanoic acid.

Another embodiment of this invention is the process for preparing the intermediate 1-(2,6-dimethoxyphenyl)propan-1-one (IV) from 2,6-dimethoxybenzoic acid by reaction with thionyl chloride followed by treatment with triethylaluminum under an inert atmosphere at −78° C. This process is much shorter and more efficient than the four-step process described in A. A. Shamshurin, et al., Chem. Abst., 62, 16102f (1965).

A further embodiment is the novel compound 1-(3-fluoro-2,6-dimethoxyphenyl)propan-1-one (V) and the process for preparing it by fluorination of compound IV with trifluoromethylhypofluorite in a halogenated solvent, such as one of the Freons.

It will be understood that in the discussion of methods of treatment which follows, references to the compounds of Formula I are meant to also include the pharmaceutically acceptable salts and the lactone form thereof.

In those instances when asymmetric centers are present, more than one stereoisomer is possible, and all possible isomeric forms are deemed to be included within the structural representations shown. Optically active (R) and (S) isomers may be resolved using conventional techniques known to the skilled artisan.

The compounds of Formula I are active as antagonists of SRS-A and of leukotriene. The activity of the compounds of Formula I can be detected and evaluated by methods known in the art. See, for example, Kadin, U.S. Pat. No. 4,296,129.

The ability of the compounds of Formula I to antagonize the effects of the leukotrienes makes them useful for inhibiting the symptoms induced by the leukotrienes in a human subject.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cyto-protective ability. These assays are; (A) an ethanol-induced lesion assay and (B) an indomethacin-induced ulcer assay and are described in EP No. 140,684.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior to up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg preferably from about 1 mg/kg to about 100 mg/kg. The dosage may be administered in single or divided individual doses.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic and organic bases.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cyto-protective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001–1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDs which are within the scope of this invention are those disclosed in EP No. 140,684.

Pharmaceutical compositions comprising the Formula I compounds may also contain inhibitors of the biosynthesis of the leukotrienes such as are disclosed in EP Nos. 138,481 (Apr. 24, 1985), 115,394 (Aug. 8, 1984), 136,893 (Apr. 10, 1985), and 140,709 (May 5, 1985), which are hereby incorporated herein by reference.

The compounds of the Formula I may also be used in combination with leukotriene antagonists such as those disclosed in EP Nos. 106,565 (Apr. 25, 1984) and 104,885 (Apr. 4, 1984) which are hereby incorporated herein by reference and others known in the art such as those disclosed in European Patent Application Nos. 56,172 (July 21, 1982) and 61,800 (Oct. 6, 1982); and in U.K. Patent Specification No. 2,058,785, which are hereby incorporated herein by reference.

Pharmaceutical compositions comprising the Formula I compounds may also contain as the second active ingredient prostaglandin antagonists such as those disclosed in EP No. 11,067 (May 28, 1980) or thromboxane antagonists such as those disclosed in U.S. Pat. No. 4,237,160 or EP No. 166,591 (Jan. 2, 1986). They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in *Nature*, vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK No. 2,038,821

(e.g., UK No. 37248 and dazoxiben hydrochloride), U.S. Pat. No. 4,217,357 (e.g., UK No. 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK-38485), or EP No. 98,690 (e.g., CV-4151).
Compounds of the present invention can be prepared according to the following methods.
SCHEME 1
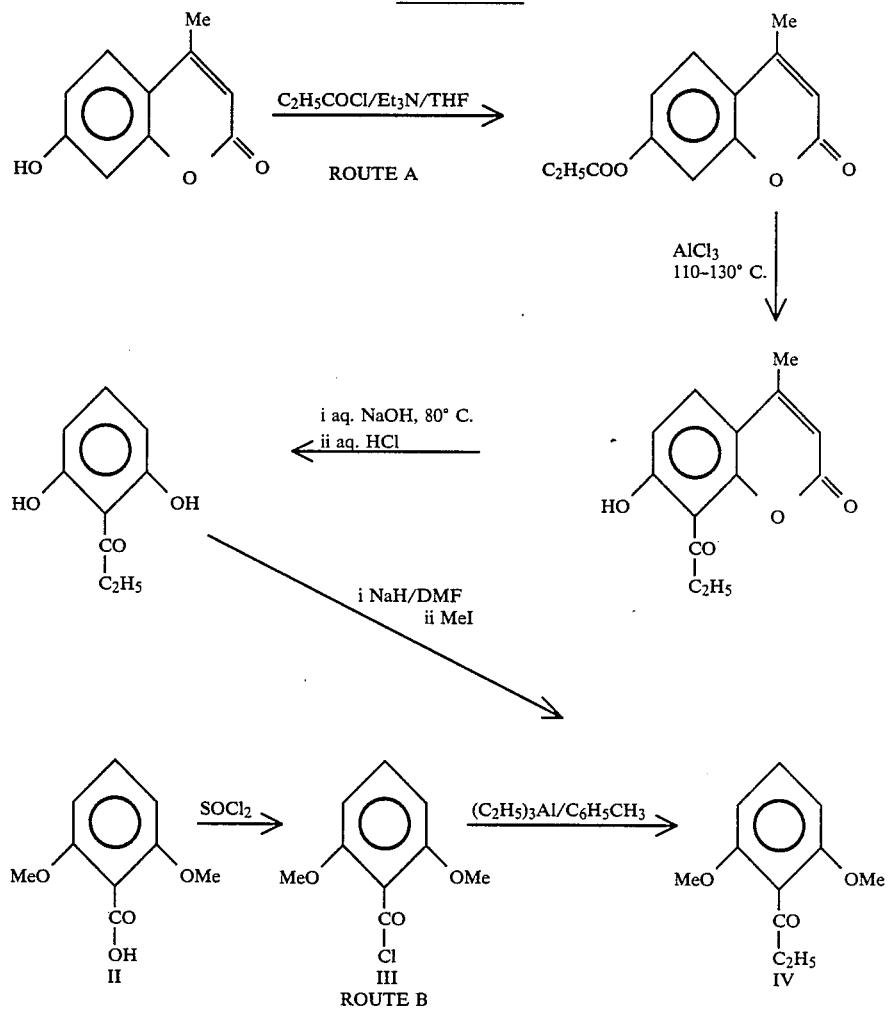
SCHEME 2
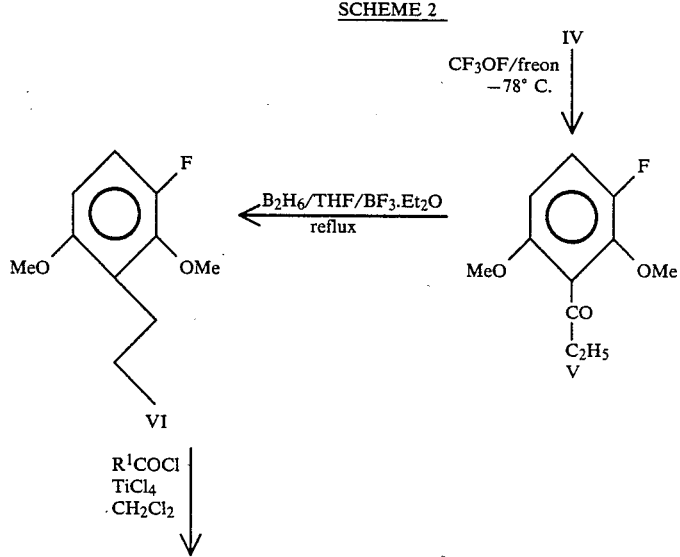

SCHEME 2
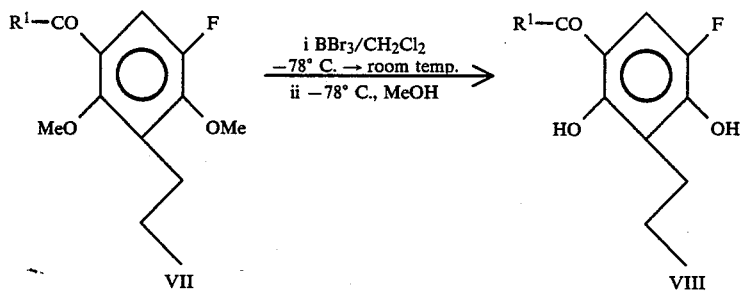
SCHEME 3
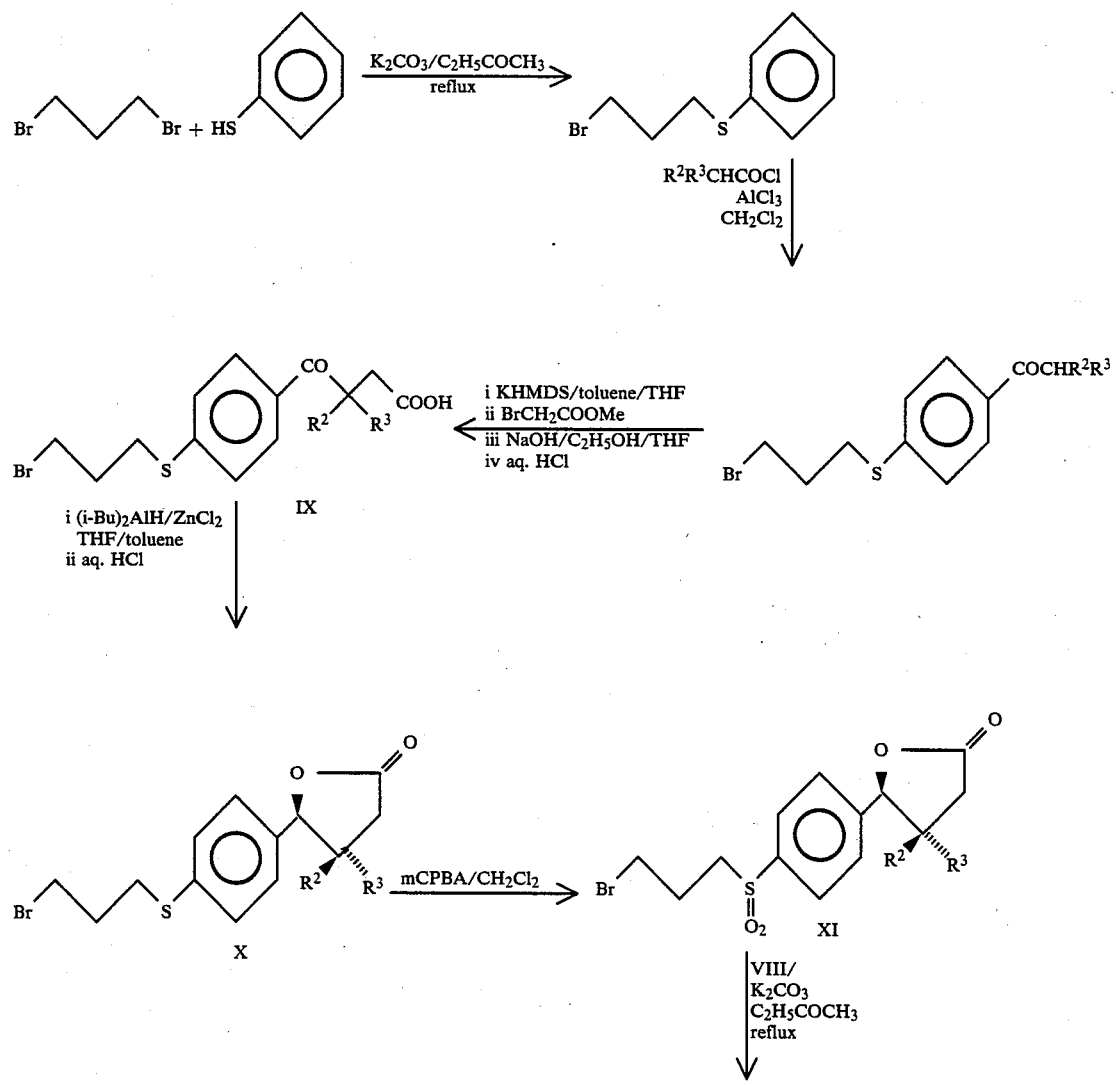

-continued
SCHEME 3

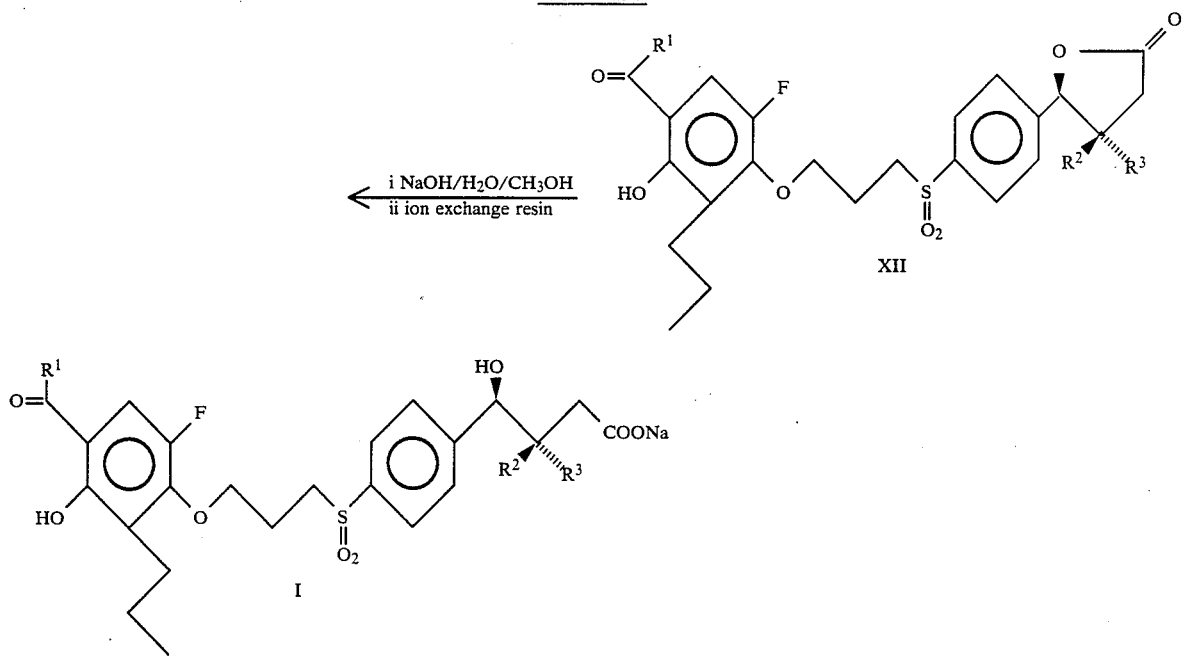

Compounds of general structure I are available by the condensation of a 1-(2,4-dihydroxy-5-fluoro-3-propylphenyl)alkan-1-one of general structure VIII and a (4R*,3S*)-4-(4-(3-bromopropylsulfonyl)phenyl)-4-hydroxy-3-alkylbutanoic acid lactone of general structure XI followed by hydrolysis of the resulting lactone XII according to Scheme 3, below.

Scheme 1

The key step in the synthesis of the fluoro-intermediate VIII is the fluorination of 1-(2,6-dimethoxy-phenyl)-propan-1-one IV. The latter can be prepared by a literature procedure (A. A. Shamshurin and Yu. M. Revenko, Izv. Akad. Nauk Moldavsk, SSR (1962), 86–97), outlined in Route A, Scheme 1, or more conveniently from 2,6-dimethoxy-benzoic acid by the newly described procedure in Route B.

2,6-Dimethoxy-benzoic acid is converted to 2,6-dimethoxybenzoyl chloride III by treatment with thionyl chloride at 70° C. for 2 hours and after removal of excess thionyl chloride the residual III is dissolved in toluene and treated at −78° C. with a solution of triethylaluminum in toluene. This procedure provides 1-(2,6-dimethoxyphenyl)propan-1-one IV in two steps from the readily available precursor II.

Scheme 2

The electrophilic fluorination of compound IV can be performed by passing trifluoromethyl hypofluorite into a stirred mixture of the compound in Freon at −78° C. The reaction is monitored frequently by thin layer chromatography to avoid over-fluorination. The crude product from the reaction is purified by column chromatography to provide 1-(3-fluoro-2,6-dimethoxyphenyl)propan-1-one V which is then reduced with borane in the presence of boron trifluoride in boiling tetrahydrofuran to give 1-fluoro-2,4-dimethoxy-3-propylbenzene VI in excellent yield. Acylation of V with an alkanoyl chloride under conventional Friedel-Crafts conditions provides a compound of general structure VII which on treatment with boron tribromide in methylene chloride at −78° C. is demethylated to yield the afore-mentioned 1-(2,4-dihydroxy-5-fluoro-3-propylphenyl)alkan-1-one of general formula VIII.

Scheme 3

Thiophenol is reacted in MEK or similar inert solvent with excess 1,3-dibromopropane and a weak anhydrous base such as $K_2CO_3$ to yield the bromopropylphenylsulfide which is then reacted with an alkanoic acid chloride in a solvent such as $CH_2Cl_2$ (or $CH_3NO_2$ or other inert solvent) in the presence of a Lewis acid such as $AlCl_3$ to yield the substituted phenyl sulfide which is then reacted in a dry solvent such as THF (or ether) with a hindered strong base, such as KHMDS (or K di-isopropylamide, etc.) at low temperature. The resulting enolate anion is reacted with methyl bromoacetate at low temperature to give the keto acid IX.

The reduction of IX by addition of the reducing agent, di-isobutylaluminum hydride in toluene, to a solution of the keto acid IX in tetrahydrofuran/toluene in the presence of one equivalent of zinc chloride, yields a (4R*,3S*)-4-(4-(3-bromopropylthio)phenyl)4-hydroxy-3-methyl-butanoic acid lactone X accompanied by ca. 1% of the (4R*,3R*)-diastereomer.

Oxidation of a compound of general structure X with about 2.5 equivalents of m-chloroperoxybenzoic acid at 0° C. in methylene chloride gives the corresponding sulfone XI which after purification by column chromatography does not contain a detectable amount of the diastereoisomeric product.

The condensation of intermediates VIII and XI is effected by potassium carbonate in refluxing 2-butanone. Hydrolysis of the resulting lactone XII with sodium hydroxide provides the final product in the form of its sodium salt as described by general structure I.

Treatment of the Na salt I with an acid, such as HCl yields the acid form of I.

The biological activity of the compounds I was compared with the activity of two structurally related compounds; namely, (4R*,3S*)-4-[4-(3-(4-acetyl-3-hydroxy-2-propylphenoxy)propylsulfonyl)phenyl]-4-hydroxy-3- methybutanoic acid and (4R*,3S*)-4-[4-(3-(4-acetyl-6-fluoro-3-hydroxy-2-propylphenoxy)propylthio)-phenyl]-4-hydroxy-3-methylbutanoic acid, Examples 77 and 93 respectively of EP No. 104,885. These reference compounds differ from I by the absence of a 2-fluoro substituent and by the degree of oxidation of the bridge sulfur respectively. The data of Table I were prepared from the following protocols.

Sensitized inbred "asthmatic rats" challenged with aerosolized antigen respond with symptoms of continuous dyspnea which is partly mediated by serotonin. The serotonin component can be completely blocked by prior treatment with 3 μg/kg of methysergide administered i.v. before challenge. These rats differ from normal rats in that they have non-specific bronchial hyper-reactivity to a number of bronchoconstrictor agents (Brunet et al, J. Immunol., 131, 434 (1983)).

Pretreatment with drugs is used to measure the decrease of the duration of continuous dyspnea and, at higher doses, to eliminate the response (piechuta et al, Immunology, 38, 385 (1979)).

Methods (1) Animals: Male and female inbred asthmatic rats were used between 10–12 weeks of age. Their weights ranged from 190–250 gm (females) and 260–400 gm (males). Rats were matched by sex and littermates between the various treatment groups. Animals were starved overnight. Water was supplied ad lib.

(2) Materials: Egg albumin (EA), grade V, crystallized and lyophilized was obtained from Sigma Chemical Co., St. Louis. Aluminum hydroxide was obtained from the Reheis Chemical Company, Chicago. Methysergide Bimaleate was supplied by Sandoz Ltd., Basel, Switzerland. Serotonin creatinine sulfate was obtained from Calbiochem-Behring Corp., La Jolla, Calif.

(3) Apparatus: The challenge and subsequent respiratory recordings were carried out in a clear plastic box with internal dimensions 10×6×4 inches. The top of the box was removable; in use, it was held firmly in place by four clamps and an airtight seal was maintained by a soft rubber gasket. Through the centre of each end of the chamber a Develbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type R Dynograph through appropriate couplers. While aerosolizing the antigen, the outlets were open and the pneumotachograph was isolated from the chamber. The outlets were closed and the pneumotachograph and the chamber were connected during the recordings of the respiratory patterns. For challenge, 2 mL of a 3% solution of antigen in saline was placed into each nebulizer and the aerosol was generated with air from a small Potter diaphragm pump operating at 10 psi and a flow of 8 liters/min.

(4) Procedure: Rats were sensitized by injecting (s.c.) 1 mL of suspension containing 1 mg albumin (EA) and 200 mg aluminum hydroxide in saline. They were used between days 12 and 24 post sensitization. Rats were exposed to aerosol of 3% EA in saline for exactly 1 minute, then their respiratory profiles were recorded for a further 30 minutes. The duration of continuous dyspnea was measured from the respiratory recordings. Compounds were generally administered either orally 1, 2, 4 or 6 hours prior to challenge or intravenously 2 minutes prior to challenge. Dose volume for oral treatments was 10 mL/kg and for i.v. treatments 1 mL/kg. Compounds were dissolved in distilled water. Methysergide bimaleate was dissolved in saline and administered intravenously at dose of 3 μg/kg 5 minutes before antigen challenge.

The sensitivity of various drug treatments were determined in terms of the decrease in duration of dyspnea in comparison with a group of vehicle treated controls. Usually, a compound was evaluated at a series of doses and an ED50 value was determined. This was defined as the dose (mg/kg) which would inhibit the duration of symptoms by 50%.

The data in Table 1 demonstrate that Compound I is significantly more active than the closely related reference compounds and that its activity in the Asthmatic Rat Assay shows good absorption by the oral route, high potency, and satisfactory duration of action.

TABLE I
COMPARATIVE EVALUATION OF COMPOUNDS IN THE ASTHMATIC RAT ASSAY

| Compound | Dose mg/kg p.o. | Hours before challenge | Inhib. of Dyspnea (%) | ED$_{50}$ p.o. (mg/kg) |
|---|---|---|---|---|
| I | 1.5 | 1 | 55 | 0.21 |
|   | 1.5 | 2 | 59 | (2 hrs) |
|   | 1.5 | 2 | 65 |   |
|   | 0.5 | 2 | 57 |   |
|   | 0.15 | 2 | 48 |   |
|   | 0.05 | 2 | 40 |   |
|   | 1.5 | 4 | 65 |   |
|   | 1.5 | 6 | 63 |   |
| Ex. 77* | 5.0 | 1 | 44 | greater than |
|   | 1.5 | 1 | 29 | 5.0 |
|   | 0.5 | 1 | 29 | (1 hr) |
|   | 0.15 | 1 | 33 |   |
| Ex. 93* | 1.5 | 1 | 26 | — |

*EP 104,885

EXAMPLE 1

1-(2,6-Dimethoxyphenyl)Propan-1-One

A. 4-Methyl-7-propanoyloxycoumarone

To a stirred mixture of 7-hydroxy-4-methylcoumarone (88.0 g, 0.5 mole), triethylamine (83.4 mL, 0.6 mole) and tetrahydrofuran (1 L) was added propanoyl chloride (46.27 g 0.5 mole) dropwise. The mixture was poured into cold 0.5 N hydrochloric acid (3 L) slowly with stirring. The solid was collected, washed with water, and dried. mp. 147° C.

Anal. Calcd. for $C_{13}H_{12}O_4$: C 67,23, H 5.21; Found C 67.03, H 5.28.

B. 7-Hydroxy-4-methyl-8-propanoylcoumarone

A mixture of Compound A (44.4 g, 0.191 mole) and aluminum chloride (101.8 g, 0.765 mole) was placed in an oil bath preheated to 110° C., and the temperature was raised to 130° C. over 2½ hours. The mixture was cooled and treated with ice (500 g) followed by concentrated hydrochloric acid (200 mL) to complete the hydrolysis of the aluminium complex. The solid was collected, washed with water and dried. The combined product from two such reactions was swished with hot ethyl acetate (600 mL), and the suspension was cooled and filtered to yield the title compound, mp. 199–200° C.

Anal. Calcd. for $C_{13}H_{12}O_4 \cdot \frac{1}{2}H_2O$: C 64.72, H, 5.43; Found: C 64.43, H 5.34.

C. 1-(2,6-Dihydroxyphenyl)propan-1-one)

To a suspension of Compound B (56.7 g, 0.244 mole) in water (330 mL) was added 10 N NaOH (104 mL), and the mixture was heated at 80° C. for 1.75 hours. The reaction mixture was cooled, and poured into a mixture of saturated NaCl (300 mL), ice (500 g), and concentrated hydrochloric acid (104 mL), slowly and with stirring. The pale yellow solid was filtered off, swished with ice-water and refiltered to yield the title compound.

An analytical sample was recrystallized from aqueous methanol, mp. 135–136° C.

Anal. Calcd. for $C_9H_{10}O_3$: C 65.05, H 6.07; Found: C 65.45, H 6.40.

D. 1-(2,6-Dimethoxyphenyl)propan-1-one

A mixture of Compound C (16.6 g, 0.1 mole) and dimethylformamide (100 mL) was treated at 0–5° C. under nitrogen with NaH (2.4 g 0.1 mole) in two portions 15 minutes apart. When hydrogen evolution had ceased, methyl iodide (6.2 mL 0.1 mole) was added. The reaction mixture became rather thick, and more dimethylformamide (67 mL) was added. More NaH (2.7 g, 0.1125 mole) was added and the mixture was stirred mechanically before the addition of more methyl iodide (7.8 mL, 0.129 mole). Stirring the mixture at room temperature for ca. 1 hour completed the reaction, and after the cautious addition of a little methanol to quench unreacted NaH, water and ether were added. The organic extract was washed with water several times, then with saturated NaCl, dried (MgSO4), and evaporated. Column chromatography (500 g of Merck AG silica gel eluted with 1:5 ethyl acetate/hexane) of the crude product gave the desired product as an oil which later solidified, mp. 43–45° C.

Anal. Calcd. for $C_{11}H_{14}O_3$: C 68.02, H 7.27; Found: C 68.10, H 7.38.

EXAMPLE 2

Alternate Synthesis Of 1-(2,6-Dimethoxyphenyl)Propan-1-One

A mixture of 2,6-dimethoxybenzoic acid (364 mg, 2 mmol) and thionyl chloride (2 mL) was warmed at 70° C. for 2 hours and then excess thionyl chloride was removed under vacuum. Toluene (5 mL) was added, and the mixture was again evaporated under vacuum. The crystalline acid chloride was dissolved in toluene (5 mL), and the solution was treated at -78° C. under argon with 1.9 M triethylaluminum (1.05 mL). The reaction mixture was allowed to attain room temperature. After 1 hour, it was again cooled to −78° C. before the dropwise addition of methanol (0.3 mL). The mixture was diluted with ether and silica gel (1.5 g) was added. The suspension was evaporated to dryness and the residue was placed on top of a column of Merck AG silica gel (25 g). Elution with 1:1:4 ethyl acetate/methylene chloride/hexane provided the product, identical with that prepared by the route of Example 1.

EXAMPLE 3

1-(5-Fluoro-2,4-Dihydroxy-3-Propylphenyl)-Ethan-1-One

A. 1-(3-Fluoro-2,6-dimethoxyphenyl)propan-1-one

Trifluoromethyl hypofluorite was bubbled through a stirred mixture of 1-(2,6-dimethoxyphenyl)- Propan-1-one (9.02 g, 46.5 mmol) and Freon (40 mL) under nitrogen at −78° C. The reaction was monitored frequently by thin layer chromatography, and passage of the gas was stopped when most of the starting material had been converted to the desired product but only a trace of the less polar difluorinated derivative had been formed. The reaction was quenched by pouring the mixture into a stirred mixture of ice and methylene chloride, and the crude product from the organic layer was submitted to column chromatography (160 g of Merck AG silica gel eluted with 1:10 ethyl acetate/hexane). The title product was the second material eluted. NMR δ (250 MHz, CDCl3, TMS) 7.03 (1H, q, ArH) 6.55 (1H, q, ArH) 3.90 (3H, d, OMe) 3.77 (3H, s, OMe) 2.76 (2H, q, CH2) 1.16 (3H, t, CH3)

B. 1-Fluoro-2,4-dimethoxy-3-propylbenzene

A solution of Compound A (5.36 g, 25.2 mmol) in dry tetrahydrofuran (28 mL) was treated with 1 M borane in tetrahydrofuran (25.2 mL), and then with boron trifluoride etherate (3.20 mL). The reaction mixture was heated at reflux for 30 min and more borane (25.2 mL) and boron trifluoride etherate (4.8 mL) were added, and stirring under reflux was resumed for a further 2 hours.

The reaction mixture was cooled in an ice-bath during the careful addition of methanol and the resulting solution was evaporated onto Merck AG silica gel (30 g). The solid was placed on top of a column of silica gel (450 g) and the title product was eluted with 1:20 ethyl acetate/hexane and was obtained as a colorless oil.

Anal. Calcd. for $C_{11}H_{15}FO_2$: C 66.65, H 7.63, F 9.58; Found: C 67.06, H 7.53, F 9.69.

C. 1-(5-Fluoro-2,4-dimethoxy-3-propylphenyl)ethan-1-one

A solution of Compound B (4.411 g, 22.3 mmol) in dry methylene chloride (50 mL) was treated at 0° C. with acetyl chloride (2.06 mL, 29 mmol), and then with titanium tetrachloride (3.07 mL, ca. 27.9 mmol) added dropwise. The mixture was stirred at 0° C. for 1 hour, and then at room temperature for 2 hours. More acetyl chloride (0.21 mL, ca. 3 mmol) was added, and stirring was continued for another 2 hours. The mixture was poured onto ice, and 6 N hydrochloric acid (5 mL) was added. The mixture was stirred, separated, and the aqueous layer was extracted wit methylene chloride. Crude product from the combined organic extract was purified by column chromatography (400 g of Merck AG silica gel eluted with 1:10 ethyl acetate/hexane) giving the title product as an oil.

Anal. Calcd. for $C_{13}H_{17}FO_3$: C 64.98, H 7.13, F 7.91; Found: C 65.06, H 7.32, F 7.97.

D. 1-(5-Fluoro-2,4-dihydroxy-3-propylphenyl)ethan-1-one

A solution of Compound C (3.223 g, 13.43 mmol) in methylene chloride (40 mL) was treated at −78° C. under argon with 1M boron tribromide solution (53 ml). The mixture was allowed to warm to room temperature; reaction was complete in 2 hours. The mixture was cooled again to −78° C. before the dropwise addition of methanol (10 mL). The solution was evaporated onto Merck AG silica gel (20 g), and the solid was placed on top of a column of silica gel (160 g). Elution with 1:5 ethyl acetate/hexane gave the title compound, mp. 129°–130° C.

Anal. Calcd. for $C_{11}H_{13}FO_3$: C 62.26, H 6.17, F 8.95; Found: C 62.23, H 6.23, F 8.86.

EXAMPLE 4

(4R*, 3S*)-4-(4-(3-Bromopropylsulphonyl)Phenyl)-4 Hydroxy-3-Methylbutanoic Acid Lactone

A. 3-Bromopropylphenylsulfide

Powdered anhydrous potassium carbonate (4.3 kg, 31 moles) was added to a mixture of 1,3-dibromopropane (6.55 kg, 32 moles), thiophenol (1.2 kg, 10.9 moles) and methylethylketone (9 L). The alkylation was carried out under a hood in a 22 liter flask equipped with a mechanical stirrer, heating mantle, and 2 reflux condensers. Nitrogen gas was passed over the top of the condensers. Within 30 minutes the mixture had generated enough heat to attain reflux. Reflux was then maintained for another 30 to 60 minutes. The mixture was permitted to come to room temperature over an 18 hour period. The solvent layer was siphoned off and filtered through celite. The salts were filtered and washed with acetone. The filtrates were concentrated. The residue was vacuum distilled. Three fractions were collected:
1. b.p. 45° C. at 0.5 mm - 1,3-dibromopropane
2. b.p. 105°–110° C. at 0.5 mm 3-bromopropylphenylsulfide
3. b.p. 184° C. at 0.7 mm–1,3-diphenyldithiopropane Anal. Calcd For $C_9H_{11}SBr$: C, 46,76; H, 4.79; S, 13.87; Br, 34.56 Found C, 46.22; H, 4.48; S, 13.89; Br, 34.20

B. 4-(3-Bromopropylthio)phenylpropan-one

To a solution of thioether A (460 g, 2 moles) and propionyl chloride (202 g, 2.2 moles) in dichloromethane (8 L) at −15° C. was added in portions of approximately 30 g over 1 hour aluminum chloride (320 g, 2.4 moles). After two hours at −15° C. the reaction mixture was quenched with ice until it became colorless, the temperature of the reaction being kept below −5° C. 1N HCl (2 L) was added and the reaction mixture was stirred until two clear phases were obtained (approximately 30 minutes). The organic layer was siphoned off and dried ($Na_2SO_4$). Evaporation afforded an oil which crystallized upon addition of hexane (2 L) and cooling in ice water bath. Filtration of the crystalline solid afforded the title compound; m.p. 40°–41° C.

C. 4-(3-Bromopropylthio)benzene-$\beta$-methyl-oxobutanoic acid

To a solution of KHMDS (potassium hexamethyldisilazane) (4.96 moles) in toluene (8 L) and THF (8 L) at −78° C. under $N_2$ was added dropwise the ketone of Step B (1.36 kg, 4.8 moles) in THF (1500 ml) over 2½ hours. The reaction mixture was stirred 1 hour at −78° C. Methyl bromoacetate (520 ml, 5.6 moles) in THF (800 ml) was added dropwise over 1-½ hours. After stirring 1 hour at −78° C. the reaction mixture was poured with stirring into 16 L of HCl (1N). The organic layer was separated and the aqueous layer was further extracted with ethyl acetate (4 L). The combined organic layers were evaporated. The residue was dissolved in a mixture of THF (6 L) and EtOH (6 L), and NaOH (3 L, 2.6M) was added. After stirring 2 hours at room temperature the homogeneous reaction mixture was concentrated in vacuo to remove THF and EtOH. The aqueous residue was extracted with ethyl acetate (2×2 L). The aqueous layer was cooled in ice-water and acidified with concentrated HCl (approximately 800 ml). Extraction with ethyl acetate (1×4 L, 1×1 L), drying ($Na_2SO_4$) and evaporation afforded the title acid as a tan, oily solid, m.p. 9220 –96° C., which was used as is in Step D.

D. (4R*,3S*)-{4-(3-Bromopropylthio)phenyl}-4-hydroxy-3-methylbutanoic acid lactone To a solution of the keto acid C (380 g, 1.1 moles) and zinc chloride (150 g, 1.1 moles) in THF (7 L) at −78° C. under $N_2$ was added dropwise over 3 hours DiBAL-H (dibutylaluminum hydride) (1.8 L of 25% solution in toluene). After stirring 1 hour at −78° C. the cold reaction mixture was poured into 1.5N HCl (8 L). The organic layer was separated and the aqueous layer was extracted with ethyl acetate (2 L). The combined organic layers were dried ($Na_2SO_4$) and evaporated in vacuo. The residue was dissolved in $CH_2Cl_2$ (1.5 L) and TFA (trifluoroacetic acid) (3 ml) was added. After stirring overnight at room temperature the reaction mixture was evaporated, dissolved in $Et_2O$ (1.5 L) washed with 1N $NaHCO_3$ (2×800 ml), dried ($Na_2SO_4$) and evaporated. Purification on flash silica gel (230–400 mesh, 1 kg) using 10:3 hexane/ethyl acetate as eluant afforded the title lactone as a slightly yellow oil.

E. (4R*,3S*)-4-(4-(3-Bromopropylsulphonyl)phenyl)-4-hydroxy-3-methylbutanoic acid lactone A solution of the lactone D (2.632 g, 8 mmol) in methylene chloride (80 mL) at 0° C. was treated with 80–85% m-chloroperbenzoic acid (4.06 g, ca. 20 mmol) added portionwise and with stirring. The reaction mixture was stirred for 1 hour at room temperature, and then cooled again to 0° C. before the addition of calcium hydroxide (4 g). The mixture was stirred at room temperature for 30 minutes, then filtered and evaporated. The residue was purified by column chromatography (280 g of silica gel eluted with 2:1 ethyl acetate/hexane) to provide the title compound.

Anal Calcd for $C_{14}H_{17}BrO_4S$: C 46.55, H 4.74, Br 22.12; S 8.88; Found C 46.17, H 4.84, Br 21.62, S 8.98

EXAMPLE 5

(4R*,3S*)-4-[4-(3-(4-Acetyl-6-Fluoro-3-Hydroxy-2-Propylphenoxy)Propylsulphonyl)Phenyl]-4-Hydroxy-3-Methylbutanoic Acid Lactone A mixture of the title ketone from Example 3 (1.37 g, 6.46 mmol), the title lactone from Example 4 (2.33 g, 6.46 mmol), anhydrous potassium carbonate (2.23 g, 16.2 mmol) and 2-butanone (28 mL) was stirred under reflux for 3.5 hours. After filtration and evaporation of the reaction mixture, the residue was submitted to flash chromatography (120 g of silica gel eluted with 2:2:3 ethyl acetate/methylene chloride/hexane) to afford the title compound as a gum which solidified to a waxy solid on standing.

NMR δ (250 MHz, $CDCl_3$, TMS) 10.61 (1H, s, OH) 7.99 (2H, d, ArH) 7.50 (2H, d, ArH) 7.27 (1H, d, ArH) 5.68 (1H, d, CH-0) 4.25 (2H, m, $CH_2$—O) 3.40 (2H, m, $CHSO_2$) 2.95 (2H, m, $CH_2CO$) 2.59 (3H, s, $CH_3CO$) 2.45 (1H, m, CHMe) 2.23 (2H, m, $CH_2$) 1.52 (2H, m, $CH_2$) 0.93 (3H, t, $CH_3$) 0.72 (3H, d, $CH_3$).

Anal Calcd for $C_{25}H_{29}FO_7S$: C 60.96, H 5.93, F 3.86, S 6.51; Found: C 60.91, H 5.76, F 3.75, S 6.83

EXAMPLE 6

Sodium (4R*,3S*)-4-[4-(3-(4-Acetyl-6-Fluoro-3-Hydroxy-2-Propylphenoxy)Ppopylsulphonyl)Phenyl]-4-Hydroxy-3-Methylbutanoate The lactone from Example 5 (2.16 g, 4.38 mmole) in methanol (50 mL) was treated with 5 N sodium hydroxide (2.19 mL), and the reaction mixture was heated under reflux for 2 hours. After addition of water, the methanol was removed by evaporation under vacuum, and the solution of sodium salt was absorbed on a column of ion exchange resin (XAD-8). After washing away excess alkali with water, the sodium salt of the product was eluted from the column with ethanol. Evaporation of the eluate, finally at 0.005 Torr, afforded the product as a solid foam.

NMR: δ (250MHz, CD$_3$COCD$_3$, TMS), 7.80 (2H, d, ArH), 7.65 (2H, d, ArH), 7.54 (lH, d, ArH), 5.02 (lH, CH-0), 4.24 (2H, t, CH$_2$O), 3.38 (2H, m, CH$_2$SO$_2$), 2.49 (3H, s, CH$_3$CO), 2.4 (4H, m, Ar-CH$_2$ and —CH$_2$COO−), 2.28 (lH, m, CH), 2.1 (2H m, CH$_2$), 1.48 (2H, m, CH$_2$), 0.88 (3H, t, CH$_3$), 0.49 (3H, d, CH$_3$).

Anal. Calcd. for C$_{25}$H$_{30}$FNaO$_8$S.H$_2$O: C 54.54; H 5.86, F 3.45, S 5.82; Found: C 54.67; H 5.98, F 3.18, S 5.79.

What is claimed is:

1. A compound of the formula:

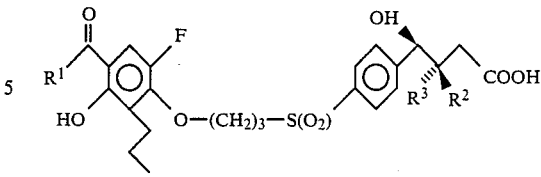

wherein R$^1$ is C$_1$–C$_6$ alkyl
R$^2$ is H or C$_1$–C$_6$ alkyl and
R$^3$ is H or C$_1$–C$_6$ alkyl and the pharmaceutically acceptable salts and γ lactone form thereof.

2. A compound of claim 1 wherein:
R$^1$ is C$_{12}$–C$_6$ alkyl;
R$^2$ is C$_1$–C$_6$ alkyl; R$^3$ is H; and
both OH and R$^2$ are on the same side of the C$_3$–C$_4$ bond.

3. A compound of claim 1 which is: (4R*,3S*)-4-[4-(3-(4-acetyl-6-fluoro-3-hydroxy-2-propylphenoxy) propylsulphonyl)phenyl]-4-hydroxy-3-methylbutanoic acid lactone.

4. A compound of claim 1 which is: Sodium (4R*,3S*)-4-[4-(3-(4-acetyl-6-fluoro-3-hydroxy-2-propylphenoxy) propylsulphonyl) phenyl]-4-hydroxy-3-methylbutanoate.

5. A compound of claim 1 which is: (4R*,3S*)-4-[4-(3-acetyl-6-fluoro-3-hydroxy-2-propylphenoxy) propylsulphonyl)phenyl]-4-hydroxy-3-methylbutanoic acid.

6. A pharmaceutical composition for inhibiting the activity of leukotriene or SRS-A comprising an effective amount of a compound of claim 1 and a pharmaceutically acceptable carrier.

* * * * *